US006755777B2

(12) United States Patent
Schweich, Jr. et al.

(10) Patent No.: US 6,755,777 B2
(45) Date of Patent: Jun. 29, 2004

(54) HEART WALL TENSION REDUCTION APPARATUS AND METHOD

(75) Inventors: Cyril J. Schweich, Jr., St. Paul, MN (US); Todd J. Mortier, Minneapolis, MN (US)

(73) Assignee: Myocor, Inc., St. Paul, MN (US)

( * ) Notice: Subject to any disclaimer, the term of this patent is extended or adjusted under 35 U.S.C. 154(b) by 0 days.

(21) Appl. No.: 10/326,585

(22) Filed: Dec. 20, 2002

(65) Prior Publication Data

US 2003/0171641 A1 Sep. 11, 2003

Related U.S. Application Data

(63) Continuation of application No. 09/985,362, filed on Nov. 2, 2001, now Pat. No. 6,514,194, which is a continuation of application No. 09/697,596, filed on Oct. 27, 2000, now Pat. No. 6,332,863, which is a continuation of application No. 09/543,155, filed on Apr. 4, 2000, now Pat. No. 6,165,120, which is a continuation of application No. 09/224,349, filed on Jan. 4, 1999, now Pat. No. 6,165,119, which is a division of application No. 08/933,456, filed on Sep. 18, 1997, now Pat. No. 5,961,440, which is a continuation-in-part of application No. 08/778,277, filed on Jan. 2, 1997, now Pat. No. 6,050,936.

(51) Int. Cl.⁷ .......................... A61B 17/12; A61M 31/00
(52) U.S. Cl. ........................................... 600/16; 600/37
(58) Field of Search ................... 607/16–18, 37; 623/3.1, 11.11, 904, 910, 913, 922; 601/153

(56) References Cited

U.S. PATENT DOCUMENTS

| | | |
|---|---|---|
| 3,019,790 A | 2/1962 | Militana |
| 3,980,086 A | 9/1976 | Kletschka et al. |
| 4,192,293 A | 3/1980 | Asrican |
| 4,261,342 A | 4/1981 | Aranguren Duo |
| 4,300,564 A | 11/1981 | Furihata |
| 4,372,293 A | 2/1983 | Vijil-Rosales |
| 4,409,974 A | 10/1983 | Freedland |
| 4,536,893 A | 8/1985 | Parravicini |
| 4,690,134 A | 9/1987 | Snyders |
| 4,705,040 A | 11/1987 | Mueller et al. |
| 4,936,857 A | 6/1990 | Kulik |
| 4,944,753 A | 7/1990 | Burgess et al. |
| 4,960,424 A | 10/1990 | Grooters |
| 4,997,431 A | 3/1991 | Isner et al. |
| 5,104,407 A | 4/1992 | Lam et al. |
| 5,106,386 A | 4/1992 | Isner et al. |
| 5,131,905 A | 7/1992 | Grooters |
| RE34,021 E | 8/1992 | Mueller et al. |
| 5,169,381 A | 12/1992 | Snyders |
| 5,192,314 A | 3/1993 | Daskalakis |
| 5,245,102 A | 9/1993 | Zarchy et al. |
| 5,250,049 A | 10/1993 | Michael |
| 5,284,488 A | 2/1994 | Sideris |
| 5,300,087 A | 4/1994 | Knoepfler |
| 5,360,444 A | 11/1994 | Kusuhara |

(List continued on next page.)

FOREIGN PATENT DOCUMENTS

| | | |
|---|---|---|
| DE | 296 19 294 | 8/1987 |
| DE | 36 14 292 | 11/1987 |
| DE | 42 34 127 | 5/1994 |

(List continued on next page.)

OTHER PUBLICATIONS

US 6,197,052, 3/2001, Cosgrove et al. (withdrawn)
Bailey et al., "Closed Intracardiac Tactile Surgery", *Disease of the Chest*, XXII:1–24, Jul. 1952.

(List continued on next page.)

*Primary Examiner*—Jeffrey R. Jastrzab
(74) *Attorney, Agent, or Firm*—Finnegan, Henderson, Farabow, Garrett & Dunner, LLP

(57) ABSTRACT

An apparatus for treatment of a failing heart by reducing the wall tension therein. In one embodiment, the apparatus includes a tension member for drawing at least two walls of a heart chamber toward each other. Methods for placing the apparatus on the heart are also provided.

50 Claims, 8 Drawing Sheets

U.S. PATENT DOCUMENTS

| | | |
|---|---|---|
| 5,385,528 A | 1/1995 | Wilk |
| 5,417,709 A | 5/1995 | Slater |
| 5,433,727 A | 7/1995 | Sideris |
| 5,450,860 A | 9/1995 | O'Connor |
| 5,452,733 A | 9/1995 | Sterman et al. |
| 5,458,574 A | 10/1995 | Machold et al. |
| 5,496,305 A | 3/1996 | Kittrell et al. |
| 5,509,428 A | 4/1996 | Dunlop |
| 5,533,958 A | 7/1996 | Wilk |
| 5,571,215 A | 11/1996 | Sterman et al. |
| 5,584,803 A | 12/1996 | Stevens et al. |
| 5,593,424 A | 1/1997 | Northrup III |
| 5,665,092 A | 9/1997 | Mangiardi et al. |
| 5,682,906 A | 11/1997 | Sterman et al. |
| 5,702,343 A | 12/1997 | Alferness |
| 5,713,954 A | 2/1998 | Rosenberg et al. |
| 5,718,725 A | 2/1998 | Sterman et al. |
| 5,755,783 A | 5/1998 | Stobie et al. |
| 5,758,663 A | 6/1998 | Wilk |
| 5,800,334 A | 9/1998 | Wilk |
| 5,800,528 A | 9/1998 | Lederman et al. |
| 5,800,531 A | 9/1998 | Cosgrove et al. |
| 5,814,097 A | 9/1998 | Sterman et al. |
| 5,849,005 A | 12/1998 | Garrison et al. |
| 5,855,601 A | 1/1999 | Bessler et al. |
| 5,855,614 A | 1/1999 | Stevens et al. |
| 5,865,791 A | 2/1999 | Whayne et al. |
| 5,902,229 A | 5/1999 | Tsitlik et al. |
| 5,928,281 A | 7/1999 | Huynh et al. |
| 5,957,977 A | 9/1999 | Melvin |
| 5,961,440 A | 10/1999 | Schweich, Jr. et al. |
| 5,961,549 A | 10/1999 | Nguyen et al. |
| 5,971,910 A | 10/1999 | Tsitlik et al. |
| 5,971,911 A | 10/1999 | Wilk |
| 5,972,022 A | 10/1999 | Huxel |
| 5,972,030 A | 10/1999 | Garrison et al. |
| 5,984,857 A | 11/1999 | Buck et al. |
| 5,984,917 A | 11/1999 | Fleischman et al. |
| 6,019,722 A | 2/2000 | Spence et al. |
| 6,024,096 A | 2/2000 | Buckberg |
| 6,024,756 A | 2/2000 | Huebsch et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,071,303 A | 6/2000 | Laufer |
| 6,077,214 A | 6/2000 | Mortier et al. |
| 6,077,218 A | 6/2000 | Alferness |
| 6,079,414 A | 6/2000 | Roth |
| 6,085,754 A | 7/2000 | Alferness et al. |
| 6,095,968 A | 8/2000 | Snyders |
| 6,102,944 A | 8/2000 | Huynh et al. |
| 6,110,100 A | 8/2000 | Talpade |
| 6,117,159 A | 9/2000 | Huebsch et al. |
| 6,123,662 A | 9/2000 | Alferness et al. |
| 6,125,852 A | 10/2000 | Stevens et al. |
| 6,126,590 A | 10/2000 | Alferness |
| 6,132,438 A | 10/2000 | Fleischman et al. |
| 6,143,025 A | 11/2000 | Stobie et al. |
| 6,155,968 A | 12/2000 | Wilk |
| 6,155,972 A | 12/2000 | Nauertz et al. |
| 6,162,168 A | 12/2000 | Schweich, Jr. et al. |
| 6,165,119 A | 12/2000 | Schweich, Jr. et al. |
| 6,165,120 A | 12/2000 | Schweich, Jr. et al. |
| 6,165,121 A | 12/2000 | Alferness |
| 6,165,122 A | 12/2000 | Alferness |
| 6,169,922 B1 | 1/2001 | Alferness et al. |
| 6,174,279 B1 | 1/2001 | Girard |
| 6,179,791 B1 | 1/2001 | Krueger |
| 6,182,664 B1 | 2/2001 | Cosgrove |
| 6,197,053 B1 | 3/2001 | Cosgrove et al. |
| 6,206,820 B1 | 3/2001 | Kazi et al. |
| 6,217,610 B1 | 4/2001 | Carpentier et al. |
| 6,221,013 B1 | 4/2001 | Panescu et al. |
| 6,221,103 B1 | 4/2001 | Melvin |
| 6,224,540 B1 | 5/2001 | Lederman et al. |
| 6,238,334 B1 | 5/2001 | Easterbrook, III et al. |
| 6,245,105 B1 | 6/2001 | Nguyen et al. |
| 6,258,021 B1 | 7/2001 | Wilk |
| 6,261,222 B1 | 7/2001 | Schweich, Jr. et al. |
| 6,269,819 B1 | 8/2001 | Oz et al. |
| 6,283,993 B1 | 9/2001 | Cosgrove et al. |
| 6,332,863 B1 | 12/2001 | Schweich, Jr. et al. |
| 6,332,864 B1 | 12/2001 | Schweich, Jr. et al. |
| 6,338,712 B2 | 1/2002 | Spence et al. |
| 6,375,608 B1 | 4/2002 | Alferness |
| 6,379,366 B1 | 4/2002 | Fleischman et al. |
| 6,406,420 B1 | 6/2002 | McCarthy et al. |
| 6,416,459 B1 | 7/2002 | Haindl |
| 6,461,366 B1 | 10/2002 | Seguin |
| 6,508,756 B1 | 1/2003 | Kung et al. |
| 6,514,194 B2 | 2/2003 | Schweich, Jr. et al. |
| 6,520,904 B1 | 2/2003 | Melvin |
| 6,572,529 B2 | 6/2003 | Wilk |
| 6,589,160 B2 | 7/2003 | Schweich, Jr. et al. |
| 6,592,619 B2 | 7/2003 | Melvin |
| 6,629,921 B1 | 10/2003 | Schweich, Jr. et al. |
| 2001/0003986 A1 | 6/2001 | Cosgrove |
| 2001/0005787 A1 | 6/2001 | Oz et al. |
| 2001/0009976 A1 | 7/2001 | Panescu et al. |
| 2001/0021874 A1 | 9/2001 | Carpentier et al. |
| 2002/0007216 A1 | 1/2002 | Melvin |
| 2002/0022880 A1 | 2/2002 | Melvin |
| 2002/0029783 A1 | 3/2002 | Stevens et al. |
| 2002/0058855 A1 | 5/2002 | Schweich, Jr. et al. |
| 2002/0065465 A1 | 5/2002 | Panescu et al. |
| 2002/0091296 A1 | 7/2002 | Alferness |
| 2002/0111533 A1 | 8/2002 | Melvin |
| 2002/0111636 A1 | 8/2002 | Fleischman et al. |
| 2002/0133055 A1 | 9/2002 | Haindl |
| 2002/0143250 A1 | 10/2002 | Panescu et al. |
| 2002/0161275 A1 | 10/2002 | Schweich, Jr. et al. |
| 2002/0169359 A1 | 11/2002 | McCarthy et al. |
| 2003/0045771 A1 | 3/2003 | Schweich, Jr. et al. |
| 2003/0166992 A1 | 9/2003 | Schweich, Jr. et al. |

FOREIGN PATENT DOCUMENTS

| | | |
|---|---|---|
| DE | 298 24 017 U1 | 6/2000 |
| EP | 0 583 012 | 2/1994 |
| EP | 0 820 729 A1 | 1/1998 |
| WO | 91/19465 | 12/1991 |
| WO | 95/06447 | 3/1995 |
| WO | 95/16476 | 6/1995 |
| WO | 96/04852 | 2/1996 |
| WO | 96/40356 | 12/1996 |
| WO | 97/14286 | 4/1997 |
| WO | 97/24082 | 7/1997 |
| WO | 97/24083 | 7/1997 |
| WO | 97/24101 | 7/1997 |
| WO | 98/03213 | 1/1998 |
| WO | 98/14136 | 4/1998 |
| WO | 98/17347 | 4/1998 |
| WO | 98/18393 | 5/1998 |
| WO | 98/26738 | 6/1998 |
| WO | 98/29041 | 7/1998 |
| WO | 98/32382 | 7/1998 |
| WO | 98/58598 | 12/1998 |
| WO | 99/00059 | 1/1999 |
| WO | 99/11201 | 3/1999 |
| WO | 99/13777 | 3/1999 |
| WO | 99/16350 | 4/1999 |
| WO | 99/30647 | 6/1999 |

| | | |
|---|---|---|
| WO | 99/44534 | 9/1999 |
| WO | 99/44680 | 9/1999 |
| WO | 99/52470 | 10/1999 |
| WO | 00/13722 | 3/2000 |
| WO | 00/18320 | 4/2000 |
| WO | 00/28912 | 5/2000 |
| WO | 00/36995 | 6/2000 |
| WO | 00/45735 | 8/2000 |
| WO | 00/62727 | 10/2000 |
| WO | 01/03608 | 1/2001 |

OTHER PUBLICATIONS

Harken et al., "The Surgical Correction of Mitral Insufficiency", Surgical forum, 4:4–7, 1953.

Harken et al., "The Surgical Correcion of Mitral Insufficiency", The Journal of Thoracic Surgery, 28:604–627, 1954.

Bailey et al. "The Surgical Correction of Mitral Insufficiency By The Use of Pericardial Grafts", The Journal of Thoracic Surgery, 28:551–603, Dec. 1954.

Kay et al., "Surgical Treatment of Mitral Insufficiency", The Journal of Thoracic Surgery, 29:618–620, 1955.

Sakakibara, "A Surgical Approach to the Correction of Mitral Insufficiency", Annals of Surgery, 142:196–203, 1955.

Glenn et al., "The Surgical Treatment of Mitral Insufficiency: The Fate of A Vascularized Transchamber Intracardiac Graft", Annals of Suger, 141:510–518, Apr. 1955.

Kay et al., "Surgical Treatment of Mitral Insufficiency", Surgery, 37:697–706, May 1955.

Lev, M.D., et al., "Single (Primitive) Ventricle," Circulation, vol. 39, May, 1969, pp. 577–591.

Edie, M.D. et al., "Surgical repair of single ventricle," The Journal of Thoracic and Cardiovascular Surgery, vol. 66, No. 3, Sep., 1973, pp. 350–360.

Boyd et al., "Tricuspid Annuloplasty," The Journal of Thoracic Cardiovascular Surgery, vol. 68, No. 3, Sep. 1974, 8 pages.

McGoon, M.D. et al., "Correction of the univentricular heart having two artrioventricular valves," The Journal of Thoracic and Cardiovascular Surgery, vol. 74, No. 2, Aug., 1977, pp. 218–226.

Doty, M.D., "Septation of the univentricular heart," The Journal of Thoracic and Cardiovascular Surgery, vol. 78, No. 3, Sep. 1979, pp. 423–430.

Schuler et al., "Temporal Response of Left Ventricular Performance to Mitral Valve Surgery," vol. 59, No. 6, Jun. 1979, pp. 1218–1231.

Feldt, M.D., "Current status of the septation procedure for univentricular heart," The Journal of Thoracic and Cardiovascular Surgery, vol. 82, No. 1, Jul., 1981, pp. 93–97.

Huikuri, "Effect of Mitral Valve Replacement on Left Ventricular Function in Mitral Regurgitation," Br. Heart J., vol. 49, 1983, pp. 328–333.

Kurlansky et al., "Adjustable Annuloplasty for Tricuspid Insufficiency," Ann. Thorac. Surg., 44:404–406, Oct. 1987.

Alonso–Lej, M.D., "Adjustable Annuloplasty for Tricuspid Insufficiency," The Annals of Thoracic Surgery, vol. 46, No. 3, Sep. 1988, 2 pages.

Chachques et al., "Latissimus Dorsi Dynamic Cardiomyoplasty," Ann. Thorac. Surg., 1989:47:600–604.

Kormos et al., "Experience with Univentricular Support in Mortally III Cardiac Transplant Candidates," Ann. Thorac. Surg., 1990:49:261–71.

Sakakibara et al., "A Muscle Powered Cardiac Assist Device for Right Ventricular Support: Total Assist or Partial Assist?," Trans. Am.Soc. Artif. Intern. Organs, vol. XXXVI, 1990, pp. 372–375.

Pitarys II et al., "Long–Term Effects of Excision of the Mitral Apparatus on Global and Regional Ventricular Function in Humans," JACC, vol. 15, No. 3, Mar. 1, 1990, pp. 557–563.

Wampler et al., "Treatment of Cardiogenic Shock with the Hemopump Left Ventricular Assist Device," Ann. Thorac. Surg., 1991:52:506–13.

McCarthy et al., "Clinical Experience with the Novacor Ventricular Assist System," J. Thorac. Cardiovas. Surg., 1991:102–578–87.

Shumacker, "Cardiac Aneurysms," The Evolution of Cardiac Surgery, 1992, pp. 159–165.

Farrar et al., "A New Skeletal Muscle Linear–Pull Energy Convertor as a Power Source for Prosthetic Support Devices," The Journal of Heart & Lung Transplantation, vol. 11, No. 5, Sep., 1992, pp. 341–349.

Savage, M.D., "Repair of left ventricular aneurysm," The Journal of Thoracic Cardiovascular Surgery, vol. 104, No. 3, Sep., 1992, pp. 752–762.

Shumacker, Jr., "Attempts to Control Mitral Regurgitation", The Evolution of Cardiac Surgery, 203–210, 1992.

Lucas et al., "Long–Term Follow–Up (12 to 35 Weeks) After Dynamic Cardiomyoplasty," JACC, vol. 22, No. 3, Sep. 1993:758–67.

Masahiro et al., "Surgery for Acquired Heart Disease/Effects of Preserving Mitral Apparatus on Ventricular Systolic Function in Mitral Valve Operations in Dogs," The Journal of Thoracic and Cardiovascular Surgery, vol. 106, No. 6, Dec. 1993, pp. 1138–1146.

Tsai et al., "Surface Modifying Additives for Improved Device–Blood Compatibility," ASAIO Journal, 1994, pp. 619–624.

Press Release dated Oct. 3, 1994, "Heartmate System Becomes First Implantable Cardiac–Assist Device to be Approved for Commercial Sale in the U.S.," 2 pages.

Press Release dated Apr. 27, 1995, "ABIOMED's Temporary Artificial Heart System Reaches 1,000 Patient Milestone; BVS–5000 in More Than 100 U.S. Medical Centers," 1 page.

Bolling et al., "Surgery for Acquired Heart Disease/Early Outcome of Mitral Valve Reconstruction in Patients with End–Stage Cardiomyopathy," The Journal of Thoracic and Cardiovascular Surgery, vol. 109, No. 4, Apr. 1995, pp. 676–683.

Bach et al., "Early Improvement in Congestive Heart Failure after Correction of Secondary Mitral Regurgitation in End-–stage Cardiomyopathy," American Heart Journal, Jun. 1995, pp. 1165–1170.

Press Release dated Jun. 9, 1995, "ABIOMED Receives Grant from National Institutes of Health to Develop a Laser Welding Technique for Tissue Repair," 1 page.

Press Release dated Aug. 11, 1995, "ABIOMED Receives Grant from NIH to Develop Disposable Bearingless Centrifugal Blood Pump," 1 page.

Press Release dated Aug. 25, 1995, "ABIOMED Wins Research Grant from NIH to Develop Suturing Instrument for Abdominal surgery," 1 page.

Press Release dated Sep. 29, 1995, "ABIOMED" Wins NIH Grant to Develop Calcification–Resistant Plastic Heart Valve, 1 page.

Press Release dated Oct. 3, 1995, "ABIOMED Wins $4.35 Million Contract from the National Heart, Lung and Blood Institutes to Develop Implantable Heart Booster," 1 page.

Carpentier et al., "Myocardial Substitution with a Stimulated Skeletal Muscle: First Successful Clinical Case," Letter to the Editor, p. 1267, Sep. 25, 1996.

Ianuzzo et al., "Preservation of the Latissimus Dorsi Muscle During Cardiomyoplasty Surgery," *J. Card. Surg.*, 1996:11:99–108.

Ianuzzo et al., "On Preconditioning of Skeletal Muscle: Application to Dynamic Cardiomyoplasty," Invited Commentary, *J. Card. Surg.*, 1996:11:109–110.

Moreira et al., "Latissimus Dorsi Cardiomyoplasty in the Treatment of Patients with Dilated Cardiomyopathy," Supplement IV Circulation, Sep. 25, 1996, 7 pgs.

Batista et al., "Partial Left Ventriculectomy to Improve Left Ventricular Function in End–Stage Heart Disease," *J. Card. Surg.*, 1996:11:96–98.

"Congestive Heart Failure in the United States: A New Epidemic" Data Fact Sheet, National Heart, Lung, and Blood Institute, National Institutes of Health, Dec. 9, 1996, pp. 1–6.

Bearson et al., "Development of a Prototype Magnetically Suspended Rotor Ventricular Assist Device," *ASAIO Journal*, 1996, pp. 275–280.

Medtronic, Inc. 1996 Annual Shareholders Report, 79 pages.

ABIOMED, Inc. Annual Report 1996, 32 pages.

Press Release dated Sep. 16, 1996, "ABIOMED Wins $8.5 Million Federal Contract to Qualify its Artificial Heart for Human Trials," 5 pages.

Press Release dated Sep. 26, 1996, "ABIOMED's Temporary Artificial Heart System Reaches 200 U.S. Medical Center Milestone," 1 page.

Press Release dated May 17, 1996, "ABIOMED Receives FDA Approval to Expand Indications for Use of Cardiac Assist System," 1 page.

"Reversible Cardiomyopathy," *Thoratec's Heartbeat*, vol. 10.2, Aug. 1996, 4 pages.

Westaby with Bosher, "Landmarks in Cardiac Surgery," 1997, pp. 198–199.

Burnett et al. "Improved Survival After Hemopump Insertion in Patients Experiencing Postcardiotomy Cardiogenic Shock During Cardiopulmonary Bypass," From the Section of Transplantation, Division of Cardiovascular Surgery, Texas Heart Institute and St. Luke's Episcopal Hospital, Houston, Texas, dated even with or prior to Jan. 2, 1997, pp. 626–628.

Phillips et al., "Hemopump Support of the Failing Heart," From the Department of Cardiovascular Medicine and Surgery, Mercy Hospital Medical Center, Des Moines, Iowa, date even with or prior to Jan. 2, 1997, pp. 629–631.

Deeb et al., "Clinical Experience with the Nimbus Pump," From the University of Michigan Medical Center Section of Thoracic Surgery and Division of Cardiology, Ann Arbor, Michigan, date even with or prior to Jan. 2, 1997, pp. 632–636.

Brochure entitled "Thoratec Ventricular Assist Device System—Because Heart Patients Come in All Sizes," date even with or prior to Jan. 2, 1997, 5 pages.

Bocchi et al., "Clinical Outcome after Surgical Remodeling of Left Ventricle in Candidates to Heart Transplantation with Idiopathic Dilated Cardiomypathy—Short Term Results," date even with or prior to Jan. 2, 1997, 1 page.

Cox, "Left Ventricular Aneurysms: Pathophysiologic Observations and Standard Resection," *Seminars In Thoracic and Cardiovascular Surgery*, vol. 9, No. 2, Apr., 1997, pp. 113–122.

McCarthy et al., "Early Results with Partial Left Ventriculectomy," From the Departments of Thoracic and Cardiovascular Surgery, Cardiology, and Transplant Center, Cleveland Clinic Foundation, presented at the 77$^{th}$ Annual Meeting of the American Association of Thoracic Surgeons, May 1997, 33 pages.

Dickstein et al., "Heart Reduction Surgery: An Analysis of the Impact on Cardiac Function," *The Journal of Thoracic and Cardiovascular Surgery*, vol. 113, No. 6, Jun. 1997, 9 pages.

Batista, MD et al., "Partial Left Ventriculectomy to Treat End–Stage Heart Disease", *Ann. Thorac. Surg.*, 64:634–8, 1997.

Melvin, "Ventricular Radius Reduction Without Restriction: A Computational Analysis," *ASAIO Journal*, 45:160–165, 1999.

Acorn Cardiovascular Highlights, Abstracts, Mar. 10, 1999.

Acorn Cardiovascular Highlights, Abstracts, Apr. 19, 1999.

Acorn Cardiovascular Highlights, Abstracts, Oct. 1, 1999.

Acorn Cardiovascular Highlights, Abstracts, Nov. 9, 1999.

Acorn Cardiovascular Executive Summary, May 2000, 7 pages.

Acorn Cardiovascular Company Overview, Jun. 2000, 6 pages.

Acorn Cardiovascular, Inc. Abstracts, Nov. 13, 2000.

"Nation's First 'Heart Jacket' Surgery to Treat Heart Failure Performed at HUP; Novel 'Cardiac Support Device' Comes to America After Promising Results in Europe," Jun. 26, 2000, 3 pages.

Acorn Cardivascular Summary, undated, 1 page.

Melvin DB, "Ventricular Radius–Reduction Without Resection A Computational Assessment", undated.

Melvin DB et al., Reduction of Ventricular Wall Tensile Stress by Geometric Remodeling Device,undated.

Acorn Cardiovascular Company Overview, undated, 2 pages.

Kay et al., "Surgical Treatment of Mitral Insufficiency", *The Journal of Thoracic Surgery*, 29:618–620, 1955.

English languageDerwent Abstract of DE 296 19 294, Jul. 1997.

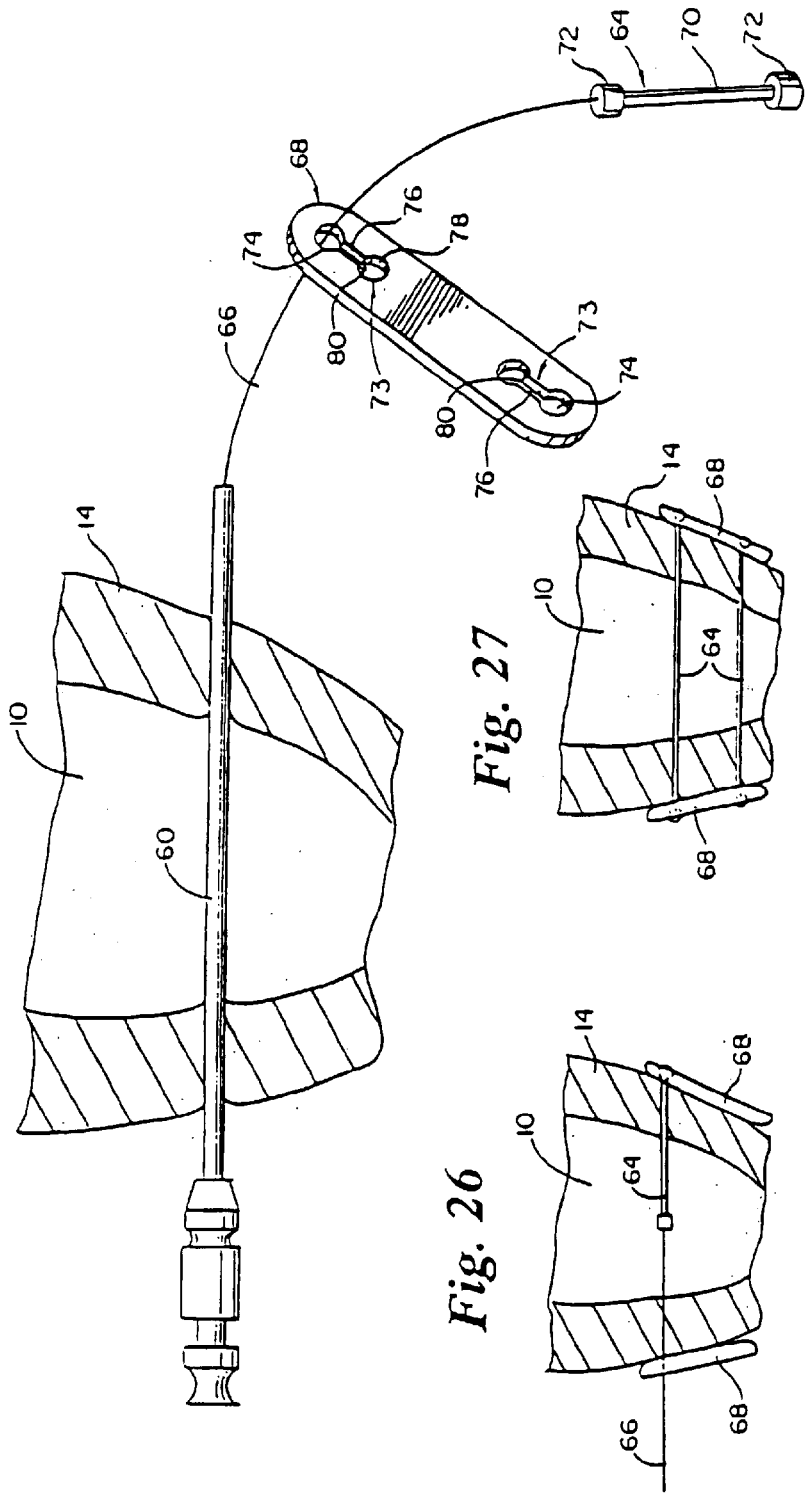

HEART WALL TENSION REDUCTION APPARATUS AND METHOD

CROSS REFERENCE TO RELATED APPLICATION

This application is a continuation of application Ser. No. 09/985,362, filed Nov. 2, 2001, now U.S. Pat. No. 6,514,194 which is a continuation of application Ser. No. 09/697,596, filed Oct. 27, 2000, now U.S. Pat. No. 6,332,863, which is a continuation of application Ser. No. 09/543,155, filed Apr. 4, 2000, now U.S. Pat. No. 6,165,120, which is a continuation of application Ser. No. 09/224,349, filed Jan. 4, 1999, now U.S. Pat. No. 6,165,119, which is a divisional of application Ser. No. 08/933,456, filed Sep. 18, 1997, now U.S. Pat. No. 5,961,440, which is a continuation-in-part of application Ser. No. 08/778,277, filed Jan. 2, 1997, now U.S. Pat. No. 6,050,936, all of which are incorporated herein by reference.

FIELD OF THE INVENTION

The present invention pertains to the field of apparatus for treatment of a failing heart. In particular, the apparatus of the present invention is directed toward reducing the wall stress in the failing heart.

BACKGROUND OF THE INVENTION

The syndrome of heart failure is a common course for the progression of many forms of heart disease. Heart failure may be considered to be the condition in which an abnormality of cardiac function is responsible for the inability of the heart to pump blood at a race commensurate with the requirements of the metabolizing tissues, or can do so only at an abnormally elevated filling pressure. There are many specific disease processes that can lead to heart failure with a resulting difference in pathophysiology of the failing heart, such as the dilatation of the left ventricular chamber. Etiologies that can lead to this form of failure include idiopathic cardiomyopathy, viral cardiomyopathy, and ischemic cardiomyopathy.

The process of ventricular dilatation is generally the result of chronic volume overload or specific damage to the myocardium. In a normal heart that is exposed to long term increased cardiac output requirements, for example, that of an athlete, there is an adaptive process of slight ventricular dilation and muscle myocyte hypertrophy. In this way, the heart fully compensates for the increased cardiac output requirements. With damage to the myocardium or chronic volume overload, however, there are increased requirements put on the contracting myocardium to such a level that this compensated state is never achieved and the heart continues to dilate.

The basic problem with a large dilated left ventricle is that there is a significant increase in wall tension and/or stress both during diastolic filling and during systolic contraction. In a normal heart, the adaptation of muscle hypertrophy (thickening) and ventricular dilatation maintain a fairly constant wall tension for systolic contraction. However, in a failing heart, the ongoing dilatation is greater than the hypertrophy and the result is a rising wall tension requirement for systolic contraction. This is felt to be an ongoing insult to the muscle myocyte resulting in further muscle damage. The increase in wall stress is also true for diastolic filling. Additionally, because of the lack of cardiac output, there is generally a rise in ventricular filling pressure from several physiologic mechanisms. Moreover, in diastole there is both a diameter increase and a pressure increase over normal, both contributing to higher wall stress levels. The increase in diastolic wall stress is felt to be the primary contributor to ongoing dilatation of the chamber.

Prior art treatments for heart failure fall into three generally categories. The first being pharmacological, for example, diuretics. The second being assist systems, for example, pumps. Finally, surgical treatments have been experimented with, which are described in more detail below.

With respect to pharmacological treatments, diuretics have been used to reduce the workload of the heart by reducing blood volume and preload. Clinically, preload is defined in several ways including left ventricular end diastolic pressure (LVEDP), or left ventricular end diastolic volume (LVEDV). Physiologically, the preferred definition is the length of stretch of the sarcomere at end diastole. Diuretics reduce extra cellular fluid which builds in congestive heart failure patients increasing preload conditions. Nitrates, arteriolar vasodilators, angiotensin converting enzyme inhibitors have been used to treat heart failure through the reduction of cardiac workload through the reduction of afterload. Afterload may be defined as the tension or stress required in the wall of the ventricle during ejection. Inotropes like digoxin are cardiac glycosides and function to increase cardiac output by increasing the force and speed of cardiac muscle contraction. These drug therapies offer some beneficial effects but do not stop the progression of the disease.

Assist devices include mechanical pumps and electrical stimulators. Mechanical pumps reduce the load on the heart by performing all or part of the pumping function normally done by the heart. Currently, mechanical pumps are used to sustain the patient while a donor heart for transplantation becomes available for the patient. Electrical stimulation such as bi-ventricular pacing have been investigated for the treatment of patients with dilated cardiomyopathy.

There are at least three surgical procedures for treatment of heart failure: 1) heart transplant; 2) dynamic cardiomyoplasty; and 3) the Batista partial left ventriculectomy. Heart transplantation has serious limitations including restricted availability of organs and adverse effects of immunosuppressive therapies required following heart transplantation. Cardiomyoplasty includes wrapping the heart with skeletal muscle and electrically stimulating the muscle to contract synchronously with the heart in order to help the pumping function of the heart. The Batista partial left ventriculectomy includes surgically remodeling the left ventricle by removing a segment of the muscular wall. This procedure reduces the diameter of the dilated heart, which in turn reduces the loading of the heart. However, this extremely invasive procedure reduces muscle mass of the heart.

SUMMARY OF THE INVENTION

The present invention pertains to a non-pharmacological, passive apparatus and method for the treatment of a failing heart. The device is configured to reduce the tension in the heart wall. It is believed to reverse, stop or slow the disease process of a failing heart as it reduces the energy consumption of the failing heart, decreases isovolumetric contraction, increases sarcomere shortening during contraction and increases isotonic shortening which in turn increases stroke volume. The device reduces wall tension during diastole and systole.

In one embodiment, the apparatus includes a tension member for drawing at least two walls of the heart chamber toward each other to reduce the radius or area of the heart chamber in at least one cross sectional plane. The tension member has anchoring members disposed at opposite ends for engagement with the heart or chamber wall.

In another embodiment, the apparatus includes a compression member for drawing at least two walls of a heart chamber toward each other. In one embodiment, the compression member includes a balloon. In another embodiment of the apparatus, a frame is provided for supporting the compression member.

Yet another embodiment of the invention includes a clamp having two ends biased toward one another for drawing at least two walls of a heart chamber toward each other. The clamp includes at least two ends having atraumatic anchoring member disposed thereon for engagement with the heart or chamber wall.

In yet another embodiment, a heart wall tension reduction apparatus is provided which includes a first tension member having two oppositely disposed ends and first and second elongate anchor members. A second tension member can be provided. One of the elongate anchors may be substituted for by two smaller anchors.

In an alternate embodiment of the heart wall tension reduction apparatus, an elongate compression member can be provided. First and second elongate lever members preferably extend from opposite ends of the compression member. A tension member extends between the first and second lever members.

The compression member of the above embodiment can be disposed exterior to, or internally of the heart. The tension member extends through the chamber or chambers to bias the lever members toward the heart.

In yet another embodiment of a heart wall tension reduction apparatus in accordance with the present invention, a rigid elongate frame member is provided. The frame member can extend through one or more chambers of the heart. One or more cantilever members can be disposed at opposite ends of the frame member. Each cantilever member includes at least one atraumatic cad disposed thereon. The atraumatic pads disposed at opposite ends of the frame member can be biased toward each other to compress the heart chamber.

One method of placing a heart wall tension apparatus or splint on a human hearts includes the step of extending a hollow needle through at least one chamber of the heart such that each end of the needle is external to the chamber. A flexible leader is connected to a first end of a tension member. A second end of the tension member is connected to an atraumatic pad. The leader is advanced through the needle from one end of he needle to the other. The leader is further advanced until the second end of the tension member is proximate the heart and the first end of the tension member is external to the heart. A second atraumatic pad is connected to the first end of the tension member such that the first and second atraumatic pads engage the heart.

An alternate method of placing the heart wall tension reduction apparatus on the heart includes the step of extending a guide member through at least one chamber of the heart such that each end of the guide member is external to the chamber. A tension member for use in this method has at least one lumen extending through at least a portion of the member. The guide member is placed in the lumen. The tension member is advanced over the guide member such that a first end of the tension member is disposed to one side of and external to the heart and a second end of the tension member is disposed to an opposite side of and external to the heart. A first atraumatic pad is connected to one end of the tension member and a second atraumatic pad is connected to the opposite end of the tension member.

Yet another method of placing a heart wall tension apparatus on a heart includes the step of extending a needle having a flexible tension member releasably connected thereto through at least one chamber of the heart such that opposite ends of the tension member are external to the chamber and exposed on opposite sides of the chamber. The needle is removed from the tension member. Then first and second atraumatic pads are connected to the tension member at opposite ends of the tension member.

BRIEF DESCRIPTION OF THE DRAWINGS

FIG. 25 is a view of the heart and needle of FIG. 24 showing a tension member being placed in the heart;

FIG. 26 is a view of the heart shown in FIG. 24 wherein oppositely disposed anchor pads are being joined by a tension member;

FIG. 27 is a view of the heart of FIG. 24, wherein two oppositely disposed anchor pads have been joined by two tension members;

DETAILED DESCRIPTION OF THE INVENTION

Figure 1:
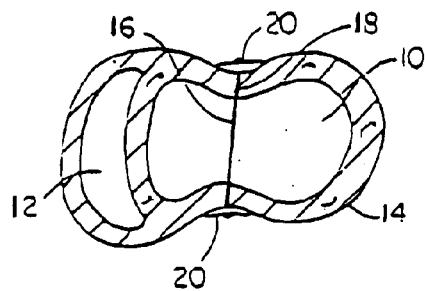
FIG. 1 is a transverse cross-section of the left and right ventricles of a human heart showing the placement of a splint in accordance with the present invention.

Referring now to the drawings wherein like reference numerals refer to like elements throughout the several views, FIG. 1 shows a transverse cross-section of a left ventricle 10 and a right ventricle 12 of a human heart 14. Extending through the left ventricle is a splint 16 including a tension member 18 and oppositely disposed anchors 20. Splint 16 as shown in FIG. 1 has been positioned to draw opposite walls of left ventricle 10 toward each other to reduce the "radius" of the left ventricular cross-section or the cross-sectional area thereof to reduce left ventricular wall stresses. It should be understood that although the splint 16 and the alternative devices disclosed herein are described in relation to the left ventricle of a human heart, these devices could also be used to reduce the radius or cross-sectional area of the other chambers of a human heart in transverse or vertical directions, or at an angle between the transverse and vertical.

Figure 2:
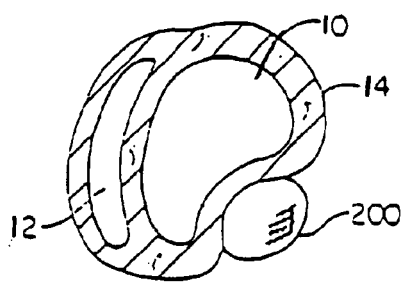
FIG. 2 is a transverse cross-section of the left and right ventricles of a human heart showing the placement of a balloon device in accordance with the present invention.

FIG. 2 discloses an alternate embodiment of the present invention, wherein a balloon 200 is deployed adjacent the left ventricle. The size and degree of inflation of the balloon can be varied to reduce the radius or cross-sectional area of left ventricle 10 of heart 14.

Figure 3:
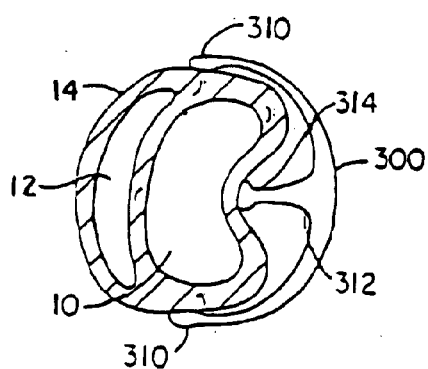
FIG. 3 is a transverse cross-section of the left and right ventricles of a human heart showing the placement of an external compression frame structure in accordance with the present invention.

FIG. 3 shows yet another alternative embodiment of the present invention deployed with respect to left ventricle 10 of human heart 14. Here a compression frame structure 300 is engaged with heart 14 at atraumatic anchor pads 310. A compression member 312 having an atraumatic surface 314 presses against a wall of left ventricle 10 to reduce the radius or cross-sectional area thereof.

Figure 4:
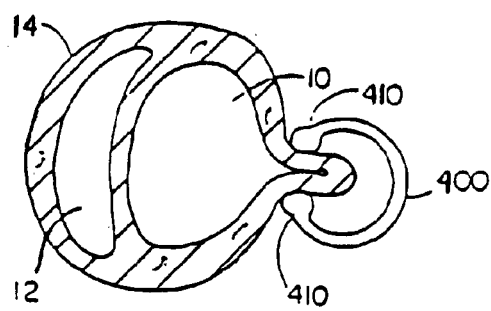
FIG. 4 is a transverse cross-section of the left and right ventricles of a human heart showing a clamp in accordance with the present invention.

FIG. 4 is a transverse cross-sectional view of human heart 14 showing yet another embodiment of the present invention. In this case a clamp 400 having atraumatic anchor pads 410 biased toward each other is shown disposed on a wall of left ventricle 10. Here the radius or cross-sectional area of left ventricle 10 is reduced by clamping off the portion of the wall between pads 410. Pads 410 can be biased toward each other and/or can be held together by a locking device.

Each of the various embodiments of the present invention disclosed in FIGS. 1–4 can be made from materials which can remain implanted in the human body indefinitely. Such biocompatible materials are well-known to those skilled in the art of clinical medical devices.

Figure 5:
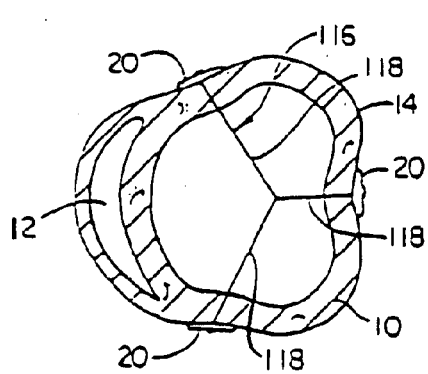
FIG. 5 is a transverse cross-section of the left and right ventricles of a human heart showing a three tension member version of the splint of FIG. 1.
Figure 6:
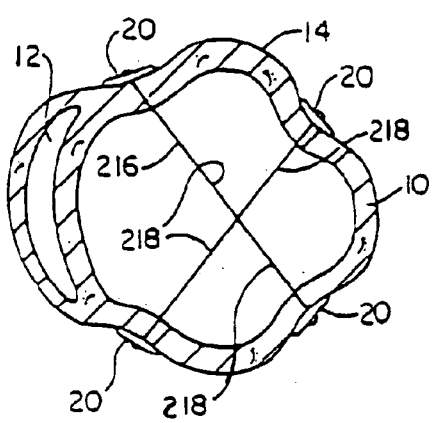
FIG. 6 is a transverse cross-section of the left and right ventricles of a human heart showing a four tension member version of the splint shown in FIG. 1.

FIG. 5 shows an alternate embodiment of the splint of FIG. 1 referred to in FIG. 5 by the numeral 116. The embodiment 116 shown in FIG. 5 includes three tension members 118 as opposed to a single tension member 18 as shown in FIG. 1. FIG. 6 shows yet another embodiment of the splint 216 having four tension members 218. It is anticipated that in some patients, the disease process of the failing heart may be so advanced that three, four or more tension members may be desirable to reduce the heart wall stresses more substantially than possible with a single tension member as shown in FIG. 1.

Figure 8:
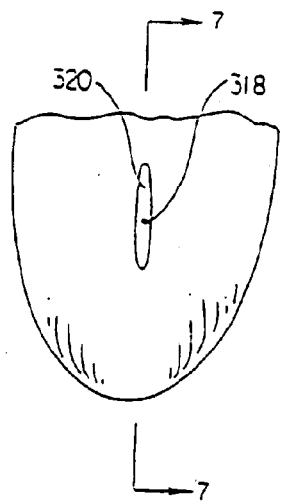
FIG. 8 is an end of the splint shown in FIG. 7.
Figure 7:
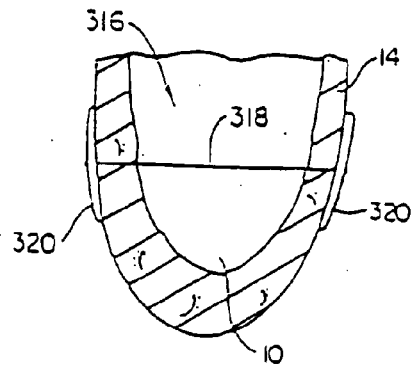
FIG. 7 is a vertical cross-sectional view of the left ventricle of a human heart showing an alternate version of the splint in accordance with the present invention.

FIG. 7 is a partial vertical cross-section of human heart 14 showing left ventricle 10. In FIG. 7, another splint embodiment 316 is shown having a tension member 318 extending through left ventricle 10. On opposite ends of tension member 318 are disposed elongate anchors or pads 320. FIG. 8 is an end view of tension member 318 showing elongate anchor 320.

Figure 9:
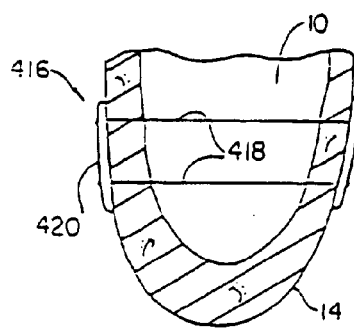
FIG. 9 is a vertical cross-sectional view of a chamber of a human heart showing another alternative embodiment of the splint in accordance with the present invention.

FIG. 9 shows another embodiment of a splint 416 disposed in a partial vertical cross-section of human heart 14. Splint 416 includes two elongate anchors or pads 420 similar to those shown in FIGS. 7 and 8. In FIG. 9, however, two tension members 418 extend through left ventricle 10 to interconnect anchors 420 on opposite sides of heart 14.

Figure 10:
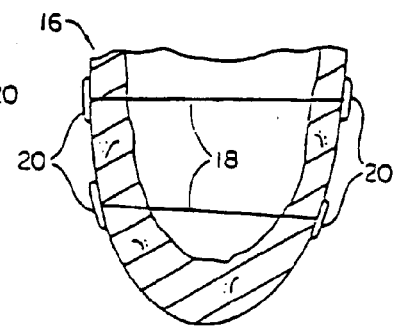
FIG. 10 is a vertical cross-section of a chamber of a human heart showing another alternative configuration of splints in accordance with the present invention.

FIG. 10 is a vertical cross section of heart 14 showing left ventricle 10. In this case, two splints 16 are disposed through left ventricle 10 and vertically spaced from each other to resemble the configuration of FIG. 9.

Figure 11:
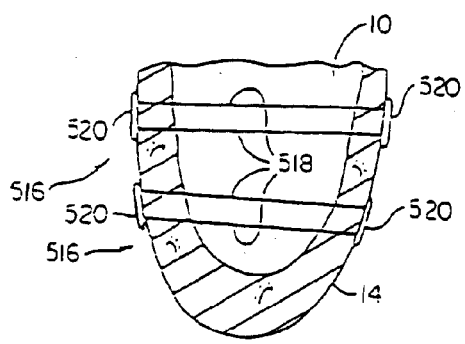
FIG. 11 is a vertical cross-sectional view of a chamber of a human heart showing another embodiment of a splint in accordance with the present invention.

FIG. 11 is a vertical cross sectional view of the left ventricle of heart 14. Two alternate embodiment splints 516 are shown extending through left ventricle 10. Each splint 516 includes two tension members 518 interconnecting two anchors or pads 520.

Figure 12:
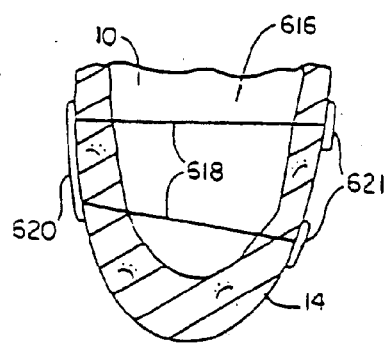
FIG. 12 is a vertical cross-sectional view of a chamber of a human heart showing another embodiment of the splint in accordance with the present invention.

FIG. 12 is yet another vertical cross sectional view of left ventricle 10 of heart 14. An alternate embodiment 616 of the splint is shown extending through left ventricle 10. Splint 616 includes an elongate anchor pad 620 and two shorter anchors or pads 621. Splint 616 includes two tension members 618. Each tension member 618 extends between anchors 620 and respective anchors 621.

Figure 13:
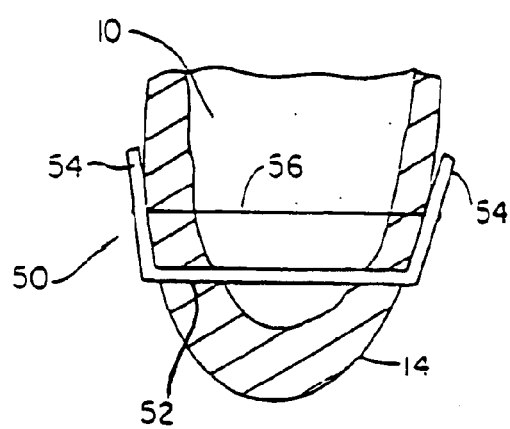
FIG. 13 is a vertical cross-sectional view of a chamber of a human heart showing a compression member version of the splint in accordance with the present invention.

FIG. 13 is a vertical cross sectional view of left ventricle 10 of heart 14. A splint 50 is shown disposed on heart 14. Splint 50 includes a compression member 52 shown extending through left ventricle 10. Opposite ends of compression member 52 are disposed exterior to left ventricle 10. Lever members 54 extend from each end of compression member 52 upwardly along the exterior surface of ventricle 10. A tension member 56 extends between lever members 54 to bias lever members 54 toward heart 14 to compress chamber 10.

Compression member 52 should be substantially rigid, but lever members 54 and to some degree compression member 52 should be flexible enough to allow tension member 56 to bias lever members 54 toward heart 14. Alternately, lever members 54 could be hinged to compression member 52 such that lever members 54 could pivot about the hinge when biased toward heart 14 by tension member 56.

Figure 14:
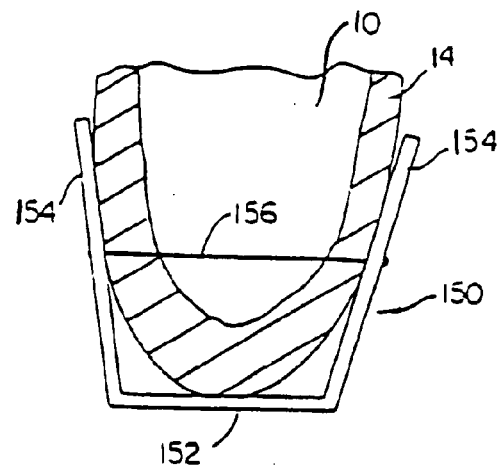
FIG. 14 is a vertical cross-sectional view of a chamber of a human heart showing another version of the splint shown in FIG. 13.

FIG. 14 shows an alternate embodiment 156 of the splint shown in FIG. 13. In this case lever members 154 are longer than members 54 as compression member 152 of splint 150 has been disposed to the exterior of left ventricle 10.

Figure 15:
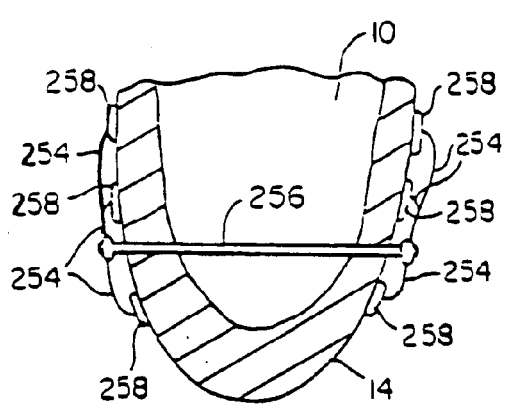
FIG. 15 is a vertical cross-sectional view of a chamber of a human heart showing a frame member version of the splint in accordance with the present invention.
Figure 16:
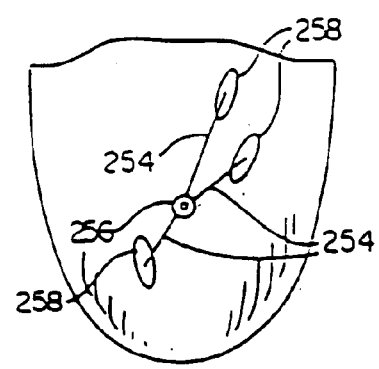
FIG. 16 is an end view of the splint of FIG. 15.

FIG. 15 is a vertical cross sectional view of left ventricle 10 of heart 14. An alternate embodiment 250 of the splint is shown on heart 14. A preferably relatively rigid frame member 256 extends through ventricle 10. Disposed on opposite ends of frame 250 are cantilever member 254. Disposed on cantilever members 254 are atraumatic pads 258. Cantilever members 254 can be positioned along frame member 256 such that atraumatic pads 258 press against heart 14 to compress chamber 10. FIG. 16 is an end view of frame member 256 showing cantilever members 254 and pads 258.

It should be understood that each of the embodiments described above should be formed from suitable biocompatible materials known to those skilled in the art. The tension members can be formed from flexible or relatively more rigid material. The compression members and frame member should be formed from generally rigid material which may flex under load, but generally hold its shape.

Figure 17:
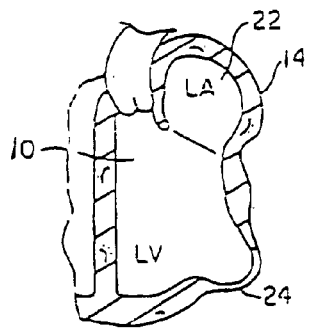
FIG. 17 is a vertical cross-section of the left ventricle and atrium, the left ventricle having scar tissue.

FIG. 17 is a partial vertical cross-section of human heart 14 showing left ventricle 10 and left atrium 22. As shown in FIG. 7, heart 14 includes a region of scar tissue 24 associated with an aneurysm or ischemia. As shown in FIG. 7, the scar tissue 24 increases the radius or cross-sectional area of left ventricle 10 in the region affected by the scar tissue. Such an increase in the radius or cross-sectional area of the left ventricle will result in greater wall stresses on the walls of the left ventricle.

Figure 18:
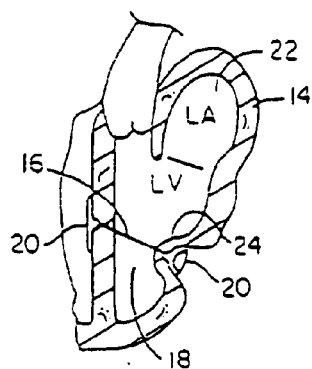
FIG. 18 is a vertical cross-section of the heart of FIG. 7 showing the splint of FIG. 1 drawing the scar tissue toward the opposite wall of the left ventricle.

FIG. 18 is a vertical cross-sectional view of the heart 14 as shown in FIG. 7, wherein a splint 16 has been placed to draw the scar tissue 24 toward an opposite wall of left ventricle 10. As a consequence of placing splint 16, the radius or cross-sectional area of the left ventricle affected by the scar tissue 24 is reduced. The reduction of this radius or cross-sectional area results in reduction in the wall stress in the left ventricular wall and thus improves heart-pumping efficiency.

Figure 19:
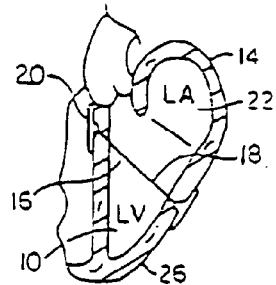
FIG. 19 is a vertical cross-section of the left ventricle and atrium of a human heart showing a version of the splint of FIG. 1 having an elongate anchor bar.

FIG. 19 is a vertical cross-sectional view of left ventricle 10 and left atrium 22 of heart 14 in which a splint 16 has been placed. As shown in FIG. 9, splint 16 includes an alternative anchor 26. The anchor 26 is preferably an elongate member having a length as shown in FIG. 9 substantially greater than its width (not shown). Anchor bar 26 might be used to reduce the radius or cross-sectional area of the left ventricle in an instance where there is generalized enlargement of left ventricle 10 such as in idiopathic dilated cardiomyopathy. In such an instance, bar anchor 26 can distribute forces more widely than anchor 20.

Figure 20:
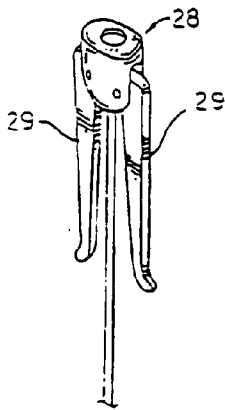
FIG. 20 is a side view of an undeployed hinged anchor member.
Figure 21:
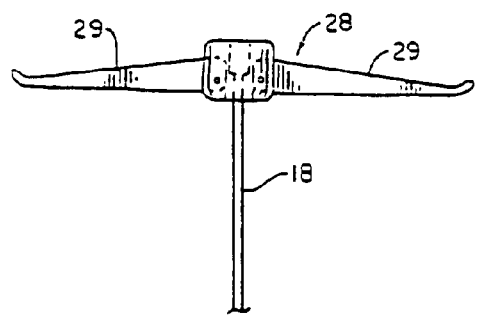
FIG. 21 is a side view of a deployed hinged anchor member of FIG. 10.

FIGS. 20 and 21 are side views of a hinged anchor 28 which could be substituted for anchors 20 in undeployed and deployed positions respectively. Anchor 28 as shown in FIG. 20 includes two legs similar to bar anchor 26. Hinged anchor 28 could include additional legs and the length of those legs could be varied to distribute the force over the surface of the heart wall. In addition there could be webbing between each of the legs to give anchor 28 an umbrella-like appearance. Preferably the webbing would be disposed on the surface of the legs which would be in contact with the heart wall.

Figure 22:
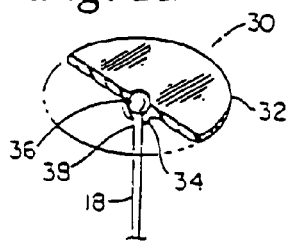
FIG. 22 is a cross-sectional view of an captured ball anchor member.

FIG. 22 is a cross-sectional view of a capture ball anchor 30. Capture ball anchor 30 can be used in place of anchor 20. Capture ball anchor 30 includes a disk portion 32 to distribute the force of the anchor on the heart wall, and a recess 34 for receiving a ball 36 affixed to an end of tension member 18. Disk 32 and recess 34 include a side groove which allows tension member 38 to be passed from an outside edge of disk 32 into recess 34. Ball 36 can then be advanced into recess 34 by drawing tension member 18 through an opening 38 in recess 34 opposite disk 32.

Figure 23:
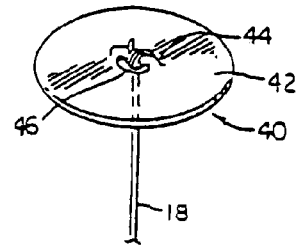
FIG. 23 is a perspective view of a cross bar anchor member.

FIG. 23 is a perspective view of a cross bar anchor 40. The cross bar anchor 40 can be used in place of anchors 20. The anchor 40 preferably includes a disk or pad portion 42 having a cross bar 44 extending over an opening 46 in pad 42. Tension member 18 can be extended through opening 46 and tied to cross bar 42 as shown.

In use, the various embodiments of the present invention are placed in or adjacent the human heart to reduce the radius or cross-section area of at least one chamber of the heart. This is done to reduce wall stress or tension in the heart or chamber wall to slow, stop or reverse failure of the heart. In the case of the splint 16 shown in FIG. 1, a canula can be used to pierce both walls of the heart and one end of the splint can be advanced through the canula from one side of the heart to the opposite side where an anchor can be affixed or deployed. Likewise, an anchor is affixed or deployed at the opposite end of splint 16.

Figure 24:
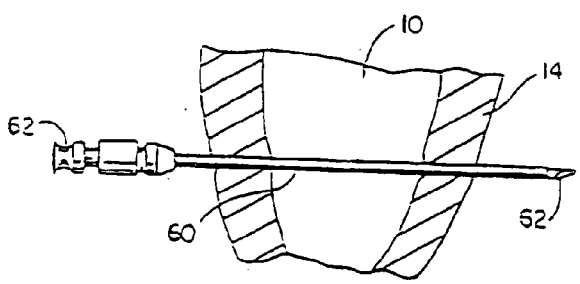
FIG. 24 is a vertical cross-sectional view of a chamber of a human heart showing a needle used for placement of splint in accordance with the present invention.

FIG. 24 is a vertical cross-sectional view of a chamber of a heart 14. A needle 60 having a stylet inserted therethrough is inserted through chamber 10. FIG. 25 shows needle 60 disposed in heart 40 as shown in FIG. 24. In FIG. 25, stylet 6 has been removed. A tension member 64 having a flexible leader 66 attached to one end of tension member 64, is threaded through needle 60 and an anchor 68.

As shown in FIG. 25, tension member 64 includes a generally elongate cylindrical shaft 70 having two generally cylindrical ends 72. Ends 72 preferably have a greater diameter than shaft 70. Also shown in FIG. 25 is a perspective view of anchor 68 showing an opening 73 extending through anchor 68. Opening 73 includes a first cylindrically shaped opening 74 extending entirely through anchor 68. The diameter of opening 74 is preferably slightly greater than the diameter of end 72 of tension member 64. A groove 76 having a width preferably slightly greater than that of shaft 70 of tension member 64 extends from opening 74 to a generally cylindrical opening 78. Generally cylindrical opening 78 has a diameter approximately equal to end 72.

Unlike opening 74, however, opening 78 includes a reduced base opening 80 which has a width approximately equal to that of groove 76. The width of the opening 80 is also less than the diameter of end 72 of tension member 64.

It can be appreciated that tension member 64 can be advanced through opening 74 until shaft 70 is disposed therein. Shaft 70 can be then slid transversely through groove 76. Tension member 64 can then be advanced further through opening 73 until end portion 72 enters opening 78 and seats against base 80.

FIG. 26 shows the view of heart 14 shown in FIG. 25. Needle 60 has been removed from heart 14. Tension member 64 has been advanced into chamber 10 and anchor 68 connected thereto is engaging the heart wall. Leader 66 has been advanced through yet another anchor 68 disposed on the opposite side of heart 14.

FIG. 27 is a view of heart 14 of FIG. 26. Two tension member 64 have been advanced through chamber 10. Each tension member has been seated in respective opening 78 against respective bases 80 to form a splint in a configuration such as that shown in FIG. 9.

It can be appreciated that each of the other tension member splints configurations can be placed on the heart in a similar manner. It can also be appreciated that anchors 68 could initially be held against the heart and needle 60 advanced through anchors 68 and chamber 10 prior to extending leader 66 through the needle.

Figure 28:
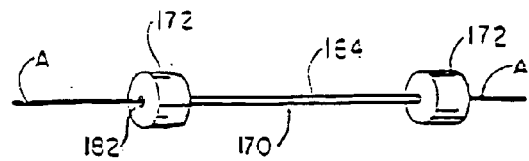
FIG. 28 is a view of a tension member having a lumen extending therethrough.

FIG. 28 is a perspective view of a tension member 164 in accordance with the present invention. Tension member 164 is similar to tension member 64 described above in that it has an elongate, generally cylindrical shaft 170 and generally cylindrical ends 172. A lumen, however, extends longitudinally through tension member 164 along axis A.

Figure 29:
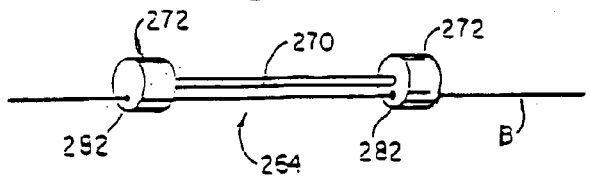
FIG. 29 is a view of a tension member having lumens extending therethrough.

FIG. 29 is a perspective view of yet another embodiment of the tension member 264. Tension member 264, is similar to tension member 164, and includes an elongate cylindrical shaft 270 and cylindrical ends 272. Lumens 282, however, extend through ends 272 aligned along axis P.

Figure 30:
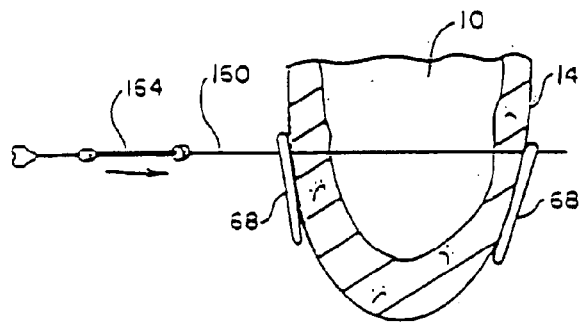
FIG. 30 is a vertical cross-sectional view of a chamber of the heart and two pads, and a needle extending therethrough.

FIG. 30 is a vertical, cross-sectional view of left ventricle 10 of heart 14. Anchors 68 have been placed on opposite sides of heart 14. A needle 160 extends through the lumen of tension member 164, left ventricle 10 and openings 73 in anchors 68. It can be appreciated that tension member 64 can be advanced through anchors 68 and left ventricle 10 and be seated within openings 78 as described above with respect to tension member 64.

Figure 31:
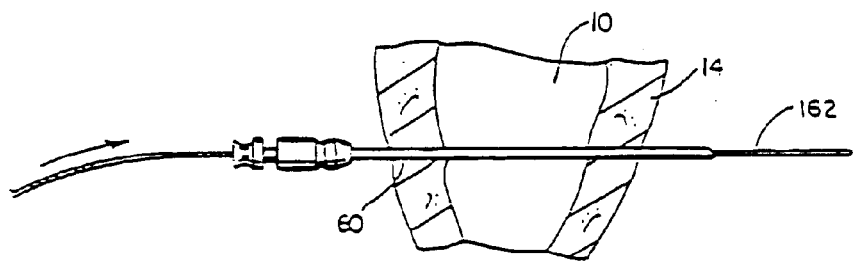
FIG. 31 is a vertical cross-sectional view of a chamber of the heart showing a guidewire extending therethrough.

FIG. 31 is a vertical, cross-sectional view of left ventricle 10 of heart 14. A needle 60 has been advanced through the wall of left ventricle 10 and a guidewire 162 has been advanced through needle 60.

Figure 32:
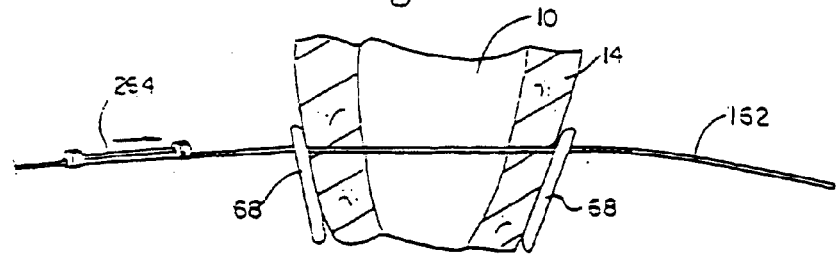
FIG. 32 is a view of the heart of FIG. 31, and two pads, and a guidewire extending therethrough.

FIG. 32 is the same view of heart 14 as shown in FIG. 32. Needle 60, however, has been removed from heart 14 while guidewire 162 remains in position. Anchors 68 have been placed on guidewire 162, on opposite sides of left ventricle 10. Tension member 264 has been threaded onto guidewire 162 through lumens 282. It can be appreciated that as discussed above with respect to tension member 164 above, tension member 264 can be advanced through left ventricle 10 such that ends 272 of tension member 264 seat in respective openings 78 against base 80.

Figure 33:
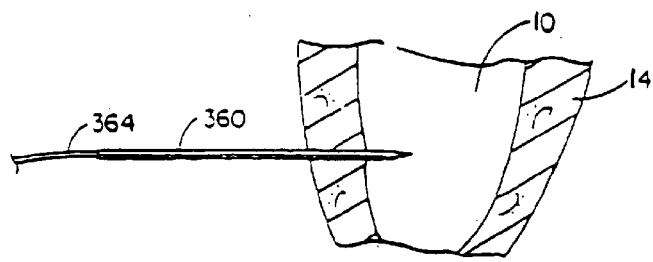
FIG. 33 is a vertical cross-sectional view of a chamber of the heart showing a needle connected to a tension member being inserted into the chamber.
Figure 34:
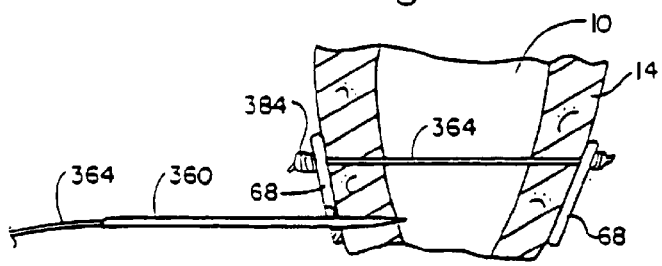
FIG. 34 is a vertical cross-sectional view of a chamber of a heart showing two anchors connected by a tension member.

FIG. 33 is a vertical, cross-sectional view of left ventricle 10 of heart 14. In FIG. 34, flexible tension member 364 has been connected to a needle 360. Needle 360 is shown being advanced into left ventricle 10 through a ventricle wall.

FIG. 34 is the same view of heart 14 as shown in FIG. 33 except that tension member 364 has been advanced entirely through left ventricle 10 and anchors 68. Knots 384 have been tied at the ends of tension member 364 to prevent the ends of tension member 364 from passing through opening 73 of anchors 68.

It can be appreciated that the methods described above to advance the tension members through the ventricles can be repeated to advance the desired number of tension members through the ventricle for a particular configuration. The length of the tension members can be determined based upon the size and condition of the patient's heart. It should also be noted that although the left ventricle has been referred to here for illustrative purposes, that the apparatus and methods of this invention can also be used to splint multiple chambers of a patient's heart as well as the right ventricle or either atrium.

Figure 35:
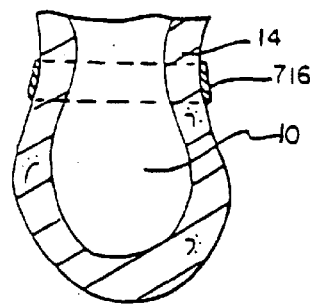
FIG. 35 is a vertical cross-sectional view of a chamber of the heart, showing a band surrounding the heart.

FIG. 35 is a vertical cross-section of left ventricle 10 of heart 14. Disposed about heart 14 is a band 716. Band 716 is shown as being sized relative to the heart such that the heart's radius or cross-sectional area in a plane parallel to the length of the band is reduced relative to the radius at that location prior to placement of the band on the heart. The length of the heart perpendicular to the band is also increased. The band may be formed from a continuous ribbon of elastomeric material or from other biocompatible materials which are sufficiently strong to provide the desired effect of heart radius reduction and lengthening.

Figure 36:
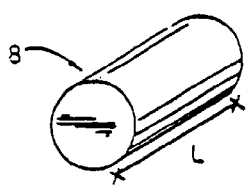
FIG. 36 is a idealized cylindrical model of a left ventricle of a human heart.

FIG. 36 is a view of a cylinder or idealized heart chamber 48 which is used to illustrate the reduction of wall stress in a heart chamber as a result of deployment of the splint in accordance with the present invention. The model used herein and the calculations related to this model are intended merely to illustrate the mechanism by which wall stress is reduced in the heart chamber. No effort is made herein to quantify the actual reduction which would be realized in any particular in vivo application.

Figure 37:
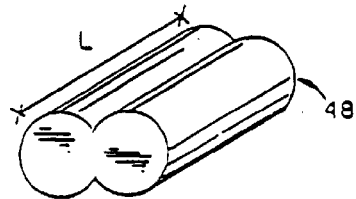
FIG. 37 is a splinted model of the left ventricle of FIG. 14.

FIG. 37 is a view of the idealized heart chamber 48 of FIG. 36 wherein the chamber has been splinted along its length L such that a "figure eight" cross-section has been formed along the length thereof. It should be noted that the perimeter of the circular transverse cross-section of the chamber in FIG. 36 is equal to the perimeter of the figure eight transverse cross-section of FIG. 37. For purposes of t is model, opposite lobes of the figure in cross-section are assumed to be mirror images.

Figure 38:
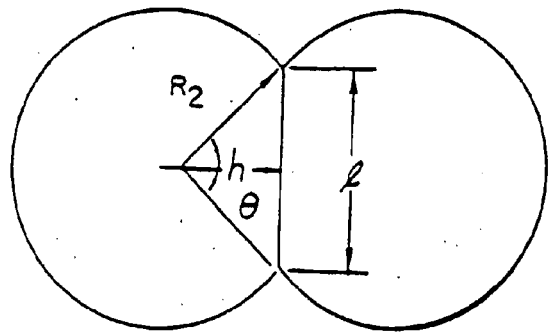
FIG. 38 is a transverse cross-sectional view of FIG. 15 showing various modeling parameters.

FIG. 38 shows various parameters of the FIG. 1 cross-section of the splinted idealized heart chamber of FIG. 37. Where l is the length of the splint between opposite walls of the chamber, $R_1$ is the radius of each lobe, $\theta$ is the angle between the two radii of one lobe which extends to opposite ends of the portion of the splint within chamber 48 and h is the height of the triangle formed by the two radii and the portion of the splint within the chamber 48 ($R_1$ is the radius of the cylinder of FIG. 36). These various parameters are related as follows:

$$h = R_2 \cos(\theta/2)$$

$$l = 2 R_2 \sin(\theta/2)$$

$$R_2 = R_1 \pi/2\pi - \theta)$$

From these relationships, the area of the figure eight cross-section can be calculated by:

$$A_2 = 2\pi(R_2)^2 (1 - \theta/2\pi) + hl$$

Where chamber 48 is unsplinted as shown in FIG. 36 $A_1$, the original cross-sectional area of the cylinder is equal to $A_2$ where θ=180°, h=0 and l=2R$_2$. Volume equals A$_2$ times length L and circumferential wall tension equals pressure within the chamber times R$_2$ times the length L of the chamber.

Thus, for example, with an original cylindrical radius of four centimeters and a pressure within the chamber of 140 mm of mercury, the wall tension T in the walls of the cylinder is 104.4 newtons. When a 3.84 cm splint is placed as shown in FIGS. 37 and 38 such that l=3.84 cm, the wall tension T is 77.33 newtons.

Figure 39:
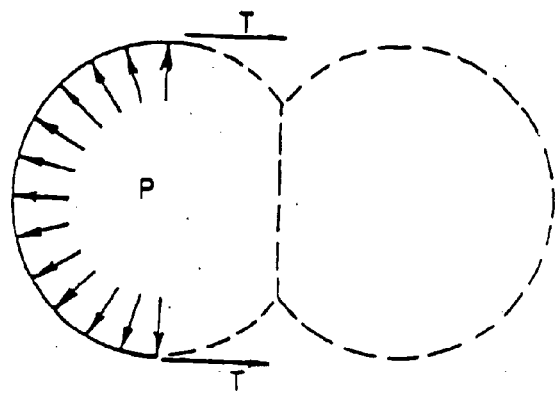
FIG. 39 is a transverse cross-section of the splinted left ventricle of FIG. 15 showing a hypothetical force distribution.
Figure 40:
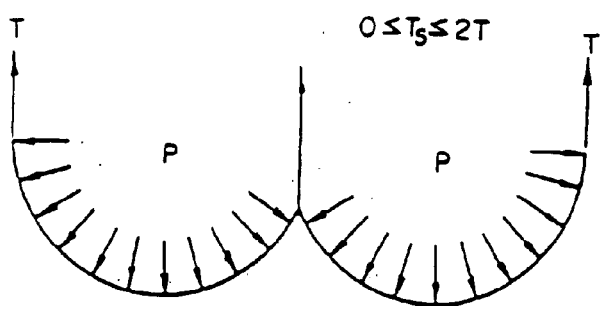
FIG. 40 is a second transverse cross-sectional view of the model left ventricle of FIG. 15 showing a hypothetical force distribution.

FIGS. 39 and 40 show a hypothetical distribution of wall tension T and pressure P for the figure eight cross-section. As θ goes from 180° to 0°, tension T$_2$ in the splint goes from 0 to a 2T load where the chamber walls carry a T load.

In yet another example, assuming that the chamber length L is a constant 10 cm, the original radius R$_1$ is 4 cm, at a 140 mmHg the tension in the walls is 74.7 N. If a 4.5 cm splint is placed such that l=4.5 cm, the wall tension will then be 52.8 N.

It will be understood that this disclosure is in many is respects, is only illustrative. Changes may be made in details, particularly in matters of shape, size, material, and arrangement of parts without exceeding the scope of the invention. Accordingly, the scope of the invention is as defined in the language of the appended claims.

What is claimed is:

1. A device for treating a heart, the device comprising:
an elongate member configured to extend externally around an apex of at least one heart chamber, the elongate member having a first end and a second end;
a first member extending from the first end of the elongate member and being configured to be positioned adjacent a first wall of the heart; and
a second member extending from the second end of the elongate member and being configured to be positioned adjacent a second wall of the heart,
wherein the device is configured to passively compress the at least one chamber during systole.

2. The device of claim 1, wherein the device is configured to alter a cross-sectional shape of the at least one chamber.

3. The device of claim 1, wherein the device is configured to reduce a radius of curvature of the at least one chamber.

4. The device of claim 1, wherein the device is configured to compress the at least one chamber during diastole.

5. The device of claim 1, wherein the device is configured to compress the at least one chamber throughout the cardiac cycle.

6. The device of claim 1, wherein the elongate member is substantially rigid.

7. The device of claim 1, wherein the first member and the second member are configured to be biased toward the heart when positioned adjacent the respective first wall and second wall.

8. The device of claim 1, further comprising a tension member configured to extend between the first member and the second member.

9. The device of claim 8, wherein the tension member is configured to extend transverse the at least one heart chamber.

10. The device of claim 8, wherein the tension member is configured to bias the first member and the second member toward the heart.

11. The device of claim 1, wherein the first member and the second member are hingedly connected to the respective first end and second end of the elongate member.

12. The device of claim 1, wherein the first member and the second member are lever members.

13. A method for treating a heart, the method comprising:
providing a substantially rigid frame;
placing the frame relative to the heart such that at least part of the frame extends externally around at least an apical portion of the heart; and
passively compressing at least one chamber of the heart via the frame.

14. The method of claim 13, further comprising altering a cross-sectional shape of the at least one chamber of the heart.

15. The method of claim 13, further comprising reducing a radius of curvature of the at least one chamber of the heart.

16. The method of claim 13, wherein the passively compressing includes passively compressing the at least one chamber during systole.

17. The method of claim 13, wherein the passively compressing includes passively compressing the at least one chamber during diastole.

18. The method of claim 13, wherein the passively compressing includes passively compressing the at least one chamber throughout the cardiac cycle.

19. The method of claim 13, further comprising drawing walls of the heart toward each other via the frame.

20. The method of claim 19, wherein the walls include walls surrounding the at least one heart chamber.

21. The method of claim 13, further comprising providing a tension member and extending the tension member transverse the at least one heart chamber and between portions of the frame.

22. The method of claim 21, further comprising extending the tension member between a first member and a second member of the frame so as to bias the first member and the second member toward the heart.

23. A method for treating a heart, the method comprising:
placing a device relative to the heart such that at least part of the device extends externally around at least an apical portion of the heart; and
at least during systole, passively compressing at least one chamber of the heart via the device.

24. The method of claim 23, further comprising altering a cross-sectional shape of the at least one chamber of the heart.

25. The method of claim 23, further comprising reducing a radius of curvature of the at least one chamber of the heart.

26. The method of claim 23, wherein the passively compressing includes passively compressing the at least one chamber throughout the cardiac cycle.

27. The method of claim 23, further comprising drawing walls of the heart toward each other via the device.

28. The method of claim 27, wherein the walls include walls surrounding the at least one chamber of the heart.

29. The method of claim 23, wherein the device includes a tension member and the method further comprises extending the tension member transverse the at least one chamber of the heart.

30. The method of claim 23, wherein the placing the device includes placing at least an additional portion of the device at least partially within the at least one chamber of the heart.

31. A device for treating a heart, the device comprising:
means for passively compressing at least one chamber of the heart at least during systole and for extending externally around an apical portion of the heart.

32. The device of claim 31, wherein the means include means for altering a cross-sectional shape of the at least one chamber of the heart.

33. The device of claim 31, wherein the means include means for reducing a radius of curvature of the at least one chamber of the heart.

34. The device of claim 31, wherein the means for passively compressing include means for passively compressing the at least one chamber throughout the cardiac cycle.

35. The device of claim 31, wherein the means include means for drawing walls of the heart toward each other.

36. The device of claim 35, wherein the walls include walls surrounding the at least one chamber of the heart.

37. The device of claim 31, wherein the means include a tension member configured to extend transverse the at least one chamber of the heart.

38. The device of claim 31, wherein the means include means configured to be placed at least partially within the at least one chamber of the heart.

39. The device of claim 31, wherein the means include substantially rigid means.

40. The device of 31, wherein the means include a frame.

41. A device for treating a heart, the device comprising:
a member configured to extend externally around an apical portion of the heart,
wherein the device is configured to passively compress at least one chamber of the heart at least during systole.

42. The device of claim 41, wherein the device is configured to alter a cross-sectional shape of the at least one chamber of the heart.

43. The device of claim 41, wherein the device is configured to reduce a radius of curvature of the at least one chamber of the heart.

44. The device of claim 41, wherein the device is configured to passively compressing the at least one chamber throughout the cardiac cycle.

45. The device of claim 41, wherein the device is configured to draw walls of the heart toward each other.

46. The device of claim 45, wherein the walls include walls surrounding the at least one chamber of the heart.

47. The device of claim 41, further comprising a tension member configured to extend transverse the at least one chamber of the heart.

48. The device of claim 41, wherein at least a portion of the device is configured to be placed at least partially within the at least one chamber of the heart.

49. The device of claim 41, wherein the member is substantially rigid.

50. The device of 41, further comprising a frame, the frame including the member.

* * * * *

UNITED STATES PATENT AND TRADEMARK OFFICE
CERTIFICATE OF CORRECTION

PATENT NO. : 6,755,777 B2 Page 1 of 1
DATED : June 29, 2004
INVENTOR(S) : Cyril J. Schweich Jr. et al.

It is certified that error appears in the above-identified patent and that said Letters Patent is hereby corrected as shown below:

Column 13,
Line 20, replace "of 31," with -- of claim 31, --;

Column 14,
Line 8, replace "compressing" with -- compress --; and
Line 22, replace "of 41," with -- of claim 41, --.

Signed and Sealed this

Thirty-first Day of August, 2004

JON W. DUDAS
*Director of the United States Patent and Trademark Office*